United States Patent [19]
Kolen et al.

[11] Patent Number: 5,800,491
[45] Date of Patent: Sep. 1, 1998

[54] THERMAL THERAPY DEVICES AND METHODS OF MAKING THE SAME

[76] Inventors: Paul T. Kolen, 139 4th St., Encinitas, Calif. 92024; Joseph F. Nebolon, 12608 Carmel Country Rd., No. 31, San Diego, Calif. 92130

[21] Appl. No.: 794,837

[22] Filed: Feb. 3, 1997

[51] Int. Cl.$^6$ .................................. A61F 5/00; A61F 7/00
[52] U.S. Cl. ............................ 607/108; 602/26; 607/112
[58] Field of Search ....................... 607/108, 109, 607/112; 602/5, 13, 26; 604/386, 387; 62/530

[56] References Cited

U.S. PATENT DOCUMENTS

| | | |
|---|---|---|
| 3,545,230 | 12/1970 | Morse . |
| 3,871,376 | 3/1975 | Kozak . |
| 3,935,099 | 1/1976 | Weaver et al. . |
| 4,243,041 | 1/1981 | Paul . |
| 4,318,248 | 3/1982 | Muldner . |
| 4,671,267 | 6/1987 | Stout . |
| 4,953,544 | 9/1990 | Hansen et al. . |
| 4,964,402 | 10/1990 | Grim et al. . |
| 5,146,630 | 9/1992 | Richard . |
| 5,150,707 | 9/1992 | Anderson . |
| 5,167,655 | 12/1992 | McCoy . |
| 5,282,994 | 2/1994 | Salyer . |
| 5,300,103 | 4/1994 | Stempel et al. . |
| 5,393,462 | 2/1995 | Avery . |
| 5,447,531 | 9/1995 | Wood . |
| 5,462,910 | 10/1995 | Ito et al. . |
| 5,466,251 | 11/1995 | Brunson et al. . |
| 5,513,629 | 5/1996 | Johnson . |
| 5,534,020 | 7/1996 | Cheney, III et al. . |
| 5,545,199 | 8/1996 | Hudson . |
| 5,565,132 | 10/1996 | Salyer . |

*Primary Examiner*—Linda C. Dvorak
*Attorney, Agent, or Firm*—Fish & Richardson P.C.

[57] ABSTRACT

A cost-effective, high heat capacity thermal therapy device is described. The therapy device includes a plurality of discrete hydrophilic absorbers hydrated with a liquid containing a substantial amount of water. The water-retention mechanism of the discrete hydrophilic absorbers allows the water to freeze under normal freezer conditions (−20° F.), to 32° F., increasing the heat capacity of the therapy device. At the same time, the therapy device remains highly pliable when frozen as a result of reduced water flow out of the absorbers during the freezing process. The therapy device also remains highly pliable through repeated freezing/melting cycles because the discrete absorbers do not lose their discrete forms when thawed.

44 Claims, 3 Drawing Sheets

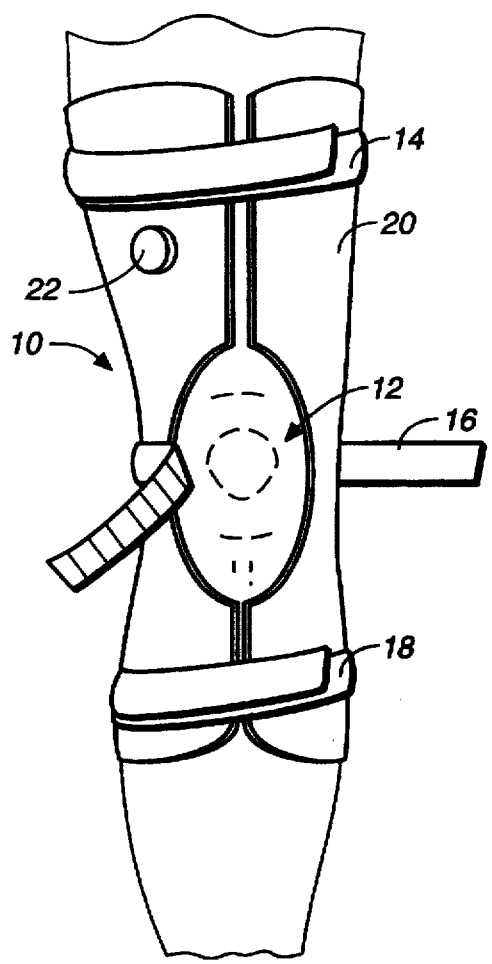
FIG._1
FIG._3
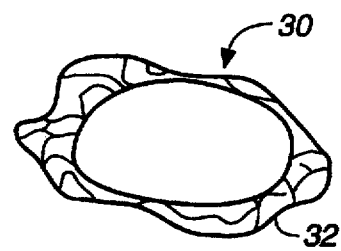
FIG._3A
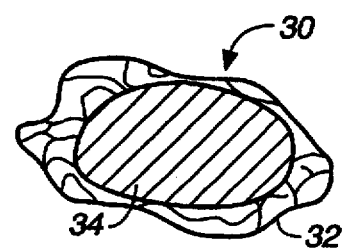
FIG._3B
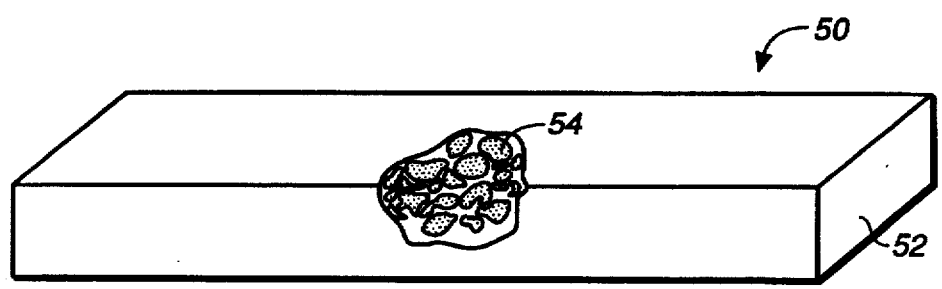
FIG._6

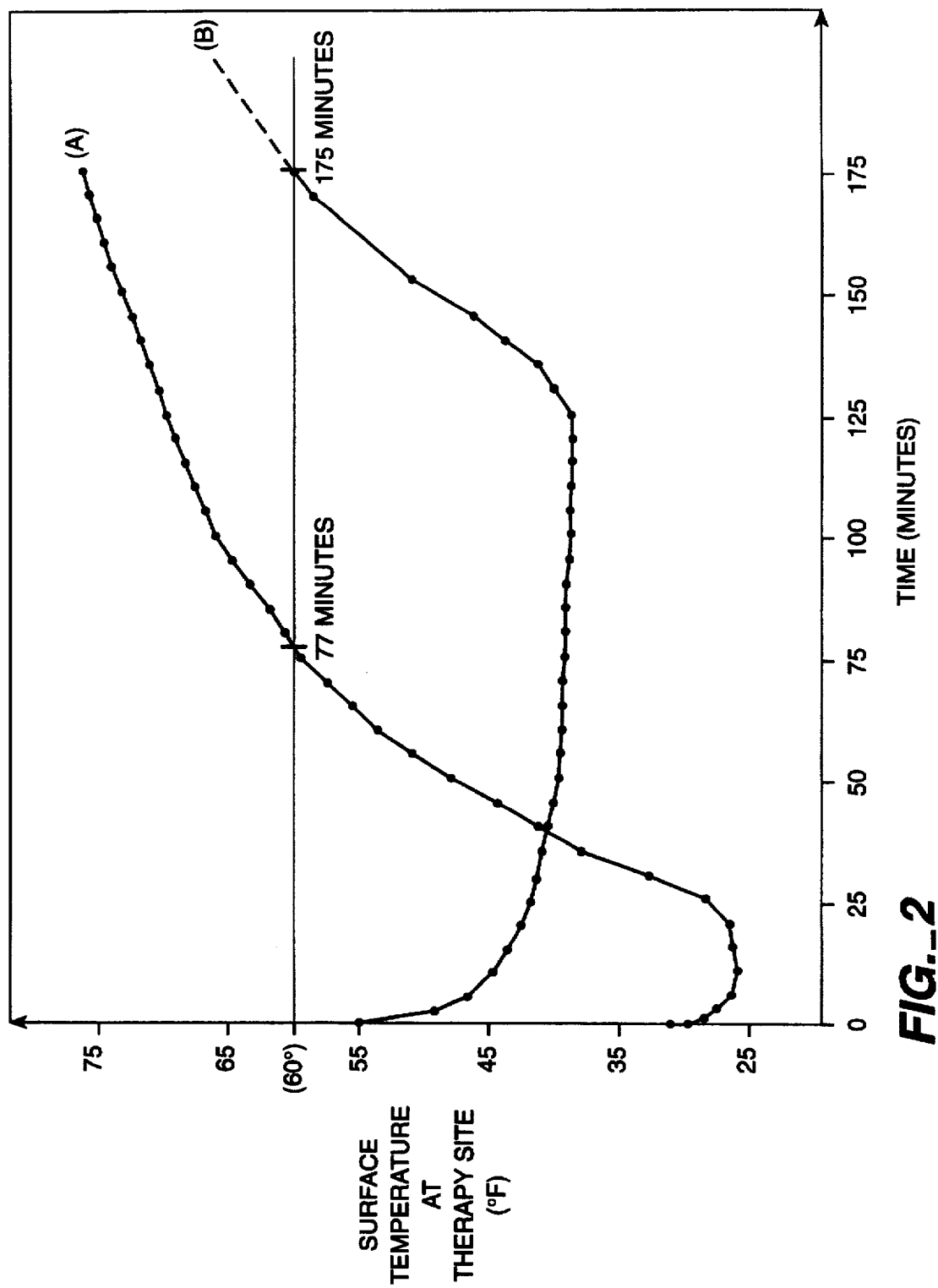
FIG._2

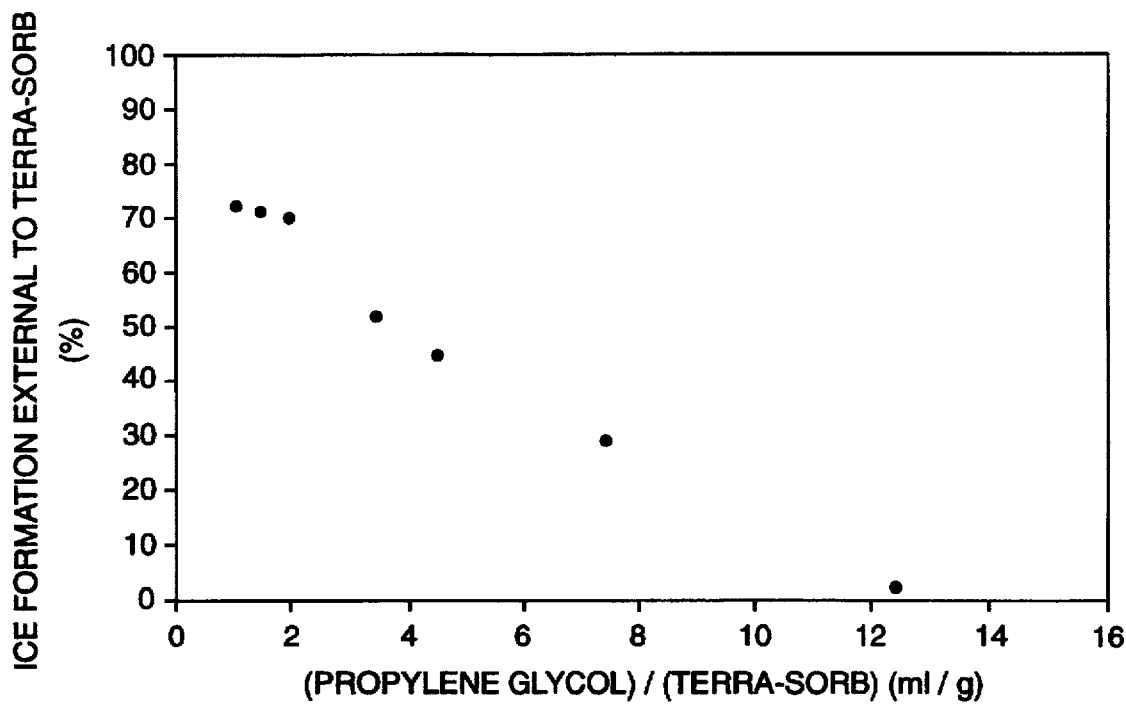
FIG._4
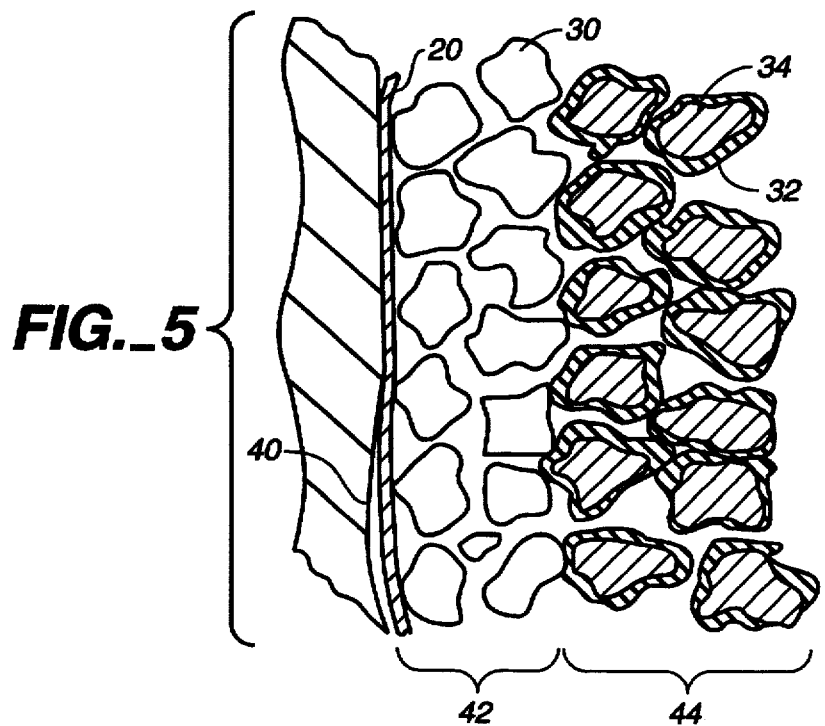
FIG._5

THERMAL THERAPY DEVICES AND METHODS OF MAKING THE SAME

BACKGROUND OF THE INVENTION

The invention relates to thermal therapy devices, and to methods of making the same.

Thermal therapy involves the application of heat or cold to tissue to heal and rehabilitate injuries, such as bruises, sprains, or other trauma to bone, muscle, ligaments, tendons, and skin. Cold therapy can be used to reduce swelling, reduce pain and promote healing of injured tissue. Heat therapy can be used to loosen joint tissue, such as ligaments and tendons, to increase range of motion, for example, before strenuous activity. Thermal therapy can be used after surgery to reduce pain and swelling and promote healing. Thermal therapy can also be used as part of an orthopedic therapy program, a sports medicine program, and to heal and rehabilitate animals, such as thoroughbred race horses.

Thermal therapy devices have been proposed that use gel materials which remain pliable at freezer temperatures (−20° F. to 32° F.) and can be reused. Such gels typically include a solution consisting of water, 25-30% propylene glycol, which limits the amount of water that freezes at normal freezer temperatures to maintain pliability, and a gelling agent, such as polyacrylamide; because a substantial amount of the solution does not undergo a liquid-to-solid phase transition, however, the heat capacity of such a gel is somewhat limited. Grim U.S. Pat. No. 4,964,402 has proposed a gel pad that includes a phase change material, such as water, encapsulated inside a thin film of vinyl, urethane, or the like, to improve the heat capacity of the gel pad.

SUMMARY OF THE INVENTION

The invention relates to pliable, high heat capacity thermal therapy devices, including a plurality of hydrated hydrophilic absorbers, which remain highly pliable through repeated freezing/melting cycles, and methods of making the same.

The invention departs from the above-described prior proposals by providing a cost-effective, high heat capacity thermal therapy device that includes a plurality of discrete hydrophilic absorbers hydrated with a liquid comprising a substantial amount of water. The water-retention mechanism of the discrete hydrophilic absorbers allows the water to freeze under normal freezer conditions (−20° F. to 32° F.), increasing the heat capacity of the therapy device. At the same time, the therapy device remains highly pliable when frozen as a result of reduced water flow out of the absorbers during the freezing process. The therapy device also remains highly pliable through repeated freezing/melting cycles because the discrete absorbers retain their discrete forms.

In preferred embodiments, the hydrophilic absorbers are formed from discrete acrylic polymer granules, such as discrete cross-linked polyacrylamide copolymer granules. These hydrophilic absorbers are characterized in that water retained therein migrates out and freezes when subjected to freezer temperatures (e.g., about 32° F. to about −20° F.) and, when thawed, melted water is reabsorbed by the hydrophilic absorbers. The hydrophilic absorbers are preferably in the size range of about 1 mm to about 6 mm when dehydrated.

In some embodiments, water flow out of the hydrophilic absorbers during the freezing process is reduced by forming the hydrating liquid from a solution of water and a humectant, such as propylene glycol, ethylene glycol, glycerin, dimethyl sulfoxide, dimethyl formamide, and combinations thereof, which decreases the mobility of water out of the hydrophilic absorbers. In some other embodiments, water flow out of the hydrophilic absorbers is reduced by suspending the hydrated absorbers within a pliable solid matrix of low water mobility. The solid matrix may be formed into a variety of predetermined shapes, such as an elongated wristrest useful for relieving pain associated with carpel tunnel syndrome.

In some embodiments, the hydrophilic absorbers are held within a flexible container that includes an air passage covered by an air permeable membrane formed from poly-tetra-fluoro-ethylene (PTFE) which has been treated with an oleophobic substance. The membrane increase the pliability of the flexible pad containing the hydrophilic absorbers by allowing air to pass into the pad as the volume of the hydrophilic absorbers shrinks during the freezing process. The air permeable membrane also enables the therapy device to remain pliable at different external pressure conditions, e.g., when the therapy device is used at high altitudes, such as in an airplane flying at high altitudes.

A plurality of hydrophobic beads may be provided within the container to increase the thermal resistance through the thermal therapy device. A coloring agent may also be included so that a patient or a therapist can visually monitor the amount of external ice that has melted and has been reabsorbed by the hydrophilic absorbers during thermal therapy treatment.

Due to the large amount of water that can undergo a liquid-to-solid phase transition under normal freezer temperatures, the invention provides a thermal therapy device with a high heat capacity. The inventive therapy device is also self-insulating so that therapeutic temperatures (i.e., temperatures below about 60° F.) can be applied to a therapy site on a patient for treatment periods lasting more than two to three times longer than a conventional gel pack of equal weight. This self-insulating feature also allows the device to optimally provide thermal therapy with a cooling rate that decrease as a function of time, which reduces the possibility of tissue damage that could result from prolonged exposure to low temperatures. The invention is also reusable; it does not leak because the hydrophilic absorbers readily absorb any liquid water resulting from the thawing of external ice; and the invention is highly cost effective due to relatively low component costs.

Other features and advantages of the invention will become apparent from the following.

BRIEF DESCRIPTION OF THE DRAWINGS

FIG. 1 is a diagrammatic view of a thermal therapy device of the invention for applying thermal therapy to a patient's knee.

FIG. 2 contains plots over time of the temperature at therapy sites on patients exposed to equal masses (246 g) of a conventional gel pad (A) and a preferred thermal therapy device of the invention (B), respectively. The therapy devices were both cooled to 0° F. prior to use.

FIGS. 3, 3A and 3B are diagrammatic cross-sectional views of a hydrophilic absorber at various times after being subjected to a freezing temperature.

FIG. 4 is a graph of the amount of external ice formation plotted as a function of the ratio of propylene glycol volume to mass of TERRA-SORB® absorbers.

FIG. 5 is a diagrammatic side view of the interface between a therapy site and a thermal therapy device of the invention.

FIG. 6 is a diagrammatic side view, partially broken away, of a wristrest of the invention.

DESCRIPTION OF THE PREFERRED EMBODIMENTS

Referring to FIG. 1, a thermal therapy device 10 applies thermal therapy to a therapy site around a patient's knee 12. Therapy device 10 is held in place by several VELCRO®, i.e., hook-and-loop type, fasteners 14, 16, 18 that allow therapy device 10 to be selectively adjusted to fit firmly, evenly and comfortably in place at the therapy site. Therapy device 10 includes a flexible thermal pad 20 that is formed from a multi-layered material, which includes an inner polyethylene layer and an outer nylon layer, and contains a plurality of discrete, non-water-soluble, hydrophilic absorbers hydrated with a liquid that consists primarily of water. A small hole is provided in pad 20 to allow air to pass in and out of pad 20; this increases the pliability of therapy device 10 and allows device 10 to be used at different altitudes. An air-permeable membrane 22 formed from a hydrophobic and oleophobic material is preferably heat-sealed over the small hole in pad 20 to retain solid and liquid components within pad 20 and to keep solids and liquids from entering pad 20. Membrane 22 may consist of a microporous membrane, such as poly-tetra-fluoro-ethylene (PTFE), which has been treated to be oleophobic, or a microporous membrane formed from acrylic, such as VERSAPOR® R which is available from Gelman Sciences Inc. of Ann Arbor, Mich. USA.

To apply cooling thermal therapy to a therapy site, therapy device 10 is pre-chilled in a freezer. When subjected to normal freezer temperatures (e.g., −20° F. to 32° F.), water follows a concentration gradient and migrates to the surface of the hydrophilic absorbers and, as a result, some of the water freezes external to the absorber. Depending upon the composition of the liquid used to hydrate the hydrophilic absorbers and the temperature of the freezer, some of the water also freezes within the hydrophilic absorbers. Because the water undergoes a liquid-to-solid phase transition, a significant amount of heat can be absorbed before the water melts and the applied therapy temperature begins to rise. This increases the period over which therapeutic temperatures (for example, temperatures below about 60° F.) can be applied to a therapy site relative to devices without phase-change materials.

It is generally preferable to vary the temperature during thermal therapy treatment to avoid discomfort and to permit long term treatment without damaging tissue. A preferred cold therapy temperature-time profile calls for a rapid reduction in the applied therapy temperature from room temperature to a low temperature (for example, about 40° F.) during an initial treatment stage. During an intermediate treatment stage, the low therapy temperature is maintained for a period of up to two to three hours. During a final treatment stage, the temperature is gradually increased until the treatment temperature reaches about 60° F.

During thermal therapy treatment, the heat load of the patient's tissue decreases which causes the skin temperature to also decrease. A conventional gel pad maintains a constant low temperature of about 25° F. until a substantial amount of the gel material has melted. As shown in FIG. 2 (A), the constant heat load applied by a conventional gel pad causes the temperature of the patient's skin to decrease to an excessively low temperature, which could damage the patient's skin. As explained below, a unique feature of therapy device 10 is that the resistance to heat flow increases over time as a result of a growing thickness of melted material between the patient's skin and the thermal core of device 10. As a result of the increasing thermal resistance of device 10 and the decreasing heat load of the treated tissue, therapy device 10 provides an essentially constant skin temperature of about 40° F. over a relatively long treatment period, as shown in FIG. 2 (B).

After therapy device 10 has warmed to a temperature of about 60° F. or so, therapy device 10 can be readily re-chilled in a freezer and reused. The many unique features of therapy device 10 enable it to be used to repeatedly apply to various therapy sites preferred temperature-time profiles of the type shown in FIG. 2 (B) for treatment periods lasting as long as 175 minutes using 250 g of hydrated hydrophilic absorbers.

One unique feature of the hydrophilic absorbers used in therapy device 10 is that they remain in discrete form through repeated cycles of water freezing and melting (i.e., unlike a gel, the hydrophilic absorbers retain their discrete identities through repeated freezing/thawing cycles). This permits therapy device 10 to be reused while remaining conformable to the shape of the therapy site on the patient's body. Referring to FIGS. 3–3B, when an initially hydrated hydrophilic absorber 30 (FIG. 3) is subjected to normal freezer temperatures (−20° F. to 32° F.), water begins to migrate out of absorber 30 and freeze on the external surface of absorber 30 (FIG. 3A); at the same time the volume of absorber 30 decreases. Under normal external pressure conditions, the water that migrates out of absorber 30 nucleates at various sites on the external surface of absorber 30 and freezes into loosely packed crystals 32 that resemble snow flakes. After a certain period of time, an equilibrium is reached whereby water stops migrating out of absorber 30 and the liquid 34 remaining within absorber 30 freezes solid (FIG. 3B), at which point therapy device 10 can be used to apply thermal therapy to a patient.

The high pliability of thermal therapy device is achieved by preventing the discrete hydrophilic absorbers from becoming interlocked by external frozen water. As explained in connection with the following exemplary embodiments, the individual hydrophilic absorbers remain in discrete form by controlling the water flow out of the hydrophilic absorbers during the freezing process.

EXAMPLE 1

In one embodiment, the hydrophilic absorbers consist of discrete cross-linked polyacrylamide copolymer granules that have been processed as described in Weaver U.S. Pat. No. 3,935,099, which is incorporated herein by reference. The hydrating liquid consists of a solution of water and humectant selected from the group consisting of propylene glycol, ethylene glycol, glycerin, dimethyl sulfoxide, dimethyl formamide, and combinations thereof.

The high pliability of this embodiment is due, in part, to the fact that the ice formation external to the hydrophilic absorbers is in the form of loosely-packed snow flakes (i.e., therapy device 10 readily takes the form of a container of crushed ice). The high pliability also results from the fact that the amount of ice that migrates out of the hydrophilic absorbers during the freezing process is controllably limited so that a significant proportion of the total water remains within the discrete hydrophilic absorbers.

As shown in FIG. 4, the amount of water that migrates out of the hydrophilic absorbers can be reduced by incorporating a humectant, such as propylene glycol, to the liquid hydrating the hydrophilic absorbers. The inventors have found that as the volume of humectant is increased relative to the mass of hydrophilic absorbers, the amount of ice that migrates out of the absorbers and freezes under normal freezer conditions uniformly decreases. The pliability of therapy device therefore increases as the amount of humectant is increased relative to the amount of hydrophilic absorbers. At some point, however, the amount of humectant is so high that the water remaining within the hydrophilic absorbers cannot freeze. In other words, the pliability of therapy device 10 must be balanced against its thermal capacity. The absolute heat capacities of different materials, including different solutions of water and propylene glycol, are provided in the following table, where $T_{Start}=-5°$ F. and $T_{End}=60°$ F.

| LIQUID | HEAT CAPACITY (CAL/GRAM) |
|---|---|
| distilled water | 103.8 |
| tap water | 101.6 |
| 93% water:7% propylene glycol | 86.2 |
| 90% water:10% propylene glycol | 80.0 |
| 85% water:15% propylene glycol | 69.5 |
| 85% water:15% propylene glycol & hydrated TERRA-SORB ® | 64.9 |
| 80% water:20% propylene glycol | 58.0 |
| Conventional Gel Pad (~75% Water:25% propylene glycol) | 45.8 |
| 70% water:30% propylene glycol | 34.1 |

As shown in FIG. 5, a unique feature of this embodiment is that it is self-insulating, which reduces the chance of harming the patient's skin and increases the period of time during which therapeutic temperatures can be applied to the therapy site. The greatest heat transfer occurs at the interface between the patient's skin 40 and the surface of thermal pad 20. Assuming therapy device 10 is applied statically, a surface layer 42 consisting of thawed hydrophilic absorbers which have reabsorbed melted ice will form near the surface of pad 20. Surface layer 42 insulates the remaining core layer 44 of ice and frozen hydrophilic absorbers from the patient's skin, increasing the thermal resistance across the skin-pad interface. The resulting increase in thermal resistance decreases the heat flow from the therapy site to pad 20, which allows the temperature at the therapy site to remain constant as the tissue heat load decreases (see, e.g., the temperature-time profile shown in FIG. 2 (B)); this reduces the possibility of damage to the patient's skin which could result from prolonged exposure to the low temperature of the thermal core of therapy device 10. Surface layer 42 also increases the length of time during which therapy device 10 can apply therapeutic temperatures (for example, below about 60° F.) to the therapy site. The use-life of therapy device 10 is also extended by the plurality of insulating air pockets created between the discrete hydrophilic absorbers.

In a preferred embodiment, the hydrophilic absorbers consist of TERRA-SORB® granules available from Plant Health Care, Inc. of Pittsburgh, Pa. USA, with a dehydrated size range of 1 mm to 6 mm; the humectant consists of propylene glycol in the amount of 1.5 ml to 17.5 ml per gram of TERRA-SORB® granules, and preferably in the amount of 3.5 ml to 4.5 ml per gram of TERRA-SORB® granules; and the amount of water in the hydrating liquid is about 50 ml to about 75 ml per gram of TERRA-SORB® granules.

A coloring agent, such as food coloring FD&C Blue No. 1, which has greater affinity for the hydrophilic absorbers than for water, can be added to the hydrating liquid to enable a patient or a therapist to monitor the heat capacity of thermal device 10. As explained above, when subjected to normal freezer temperatures, some water migrates out of the hydrophilic absorbers and freezes as white ice crystals; the remaining water along with the coloring agent freeze within the hydrophilic absorbers. As the external ice thaws and becomes reabsorbed by the hydrophilic absorbers, the amount of external white ice crystals gradually decreases until all of the ice has melted. It is this variation in color that allows a patient or a therapist to visually monitor the status of therapy device 10 during treatment.

EXAMPLE 2

In another embodiment, a plurality of pre-hydrated hydrophilic absorbers are contained within a pliable solid matrix which is characterized by a water mobility that is sufficiently low that very little water migrates out of the hydrophilic absorbers during freezing. For this reason, the discrete hydrophilic absorbers do not freeze together as a solid unit. In this embodiment, a surrounding flexible layer, such as thermal pad 20 (FIG. 1), is not needed, but may be used for some applications. Because the water flow out of the hydrophilic absorbers is controlled by the low water mobility of the solid matrix, the hydrating liquid can consist primarily of water.

The solid matrix can be molded into a variety of shapes. For example, as shown in FIG. 6, a thermal therapy device 50 can be formed from a pliable solid matrix 52 which incorporates a plurality of pre-hydrated hydrophilic absorbers 54 and is molded in the form of a wristrest that can be used when typing. Thermal therapy device 50 can be chilled in a freezer and used to relieve pain associated with, for example, carpel tunnel syndrome. The thermal capacity of the wristrest is increased by the frozen water retained within the hydrophilic absorbers, while the original pliability of the solid matrix is not compromised because the hydrophilic absorbers do not freeze together as a solid unit.

In a preferred embodiment, the pliable solid matrix is formed from moldable gel materials made according to the method described in Stout U.S. Pat. No. 4,671,267, which is incorporated herein by reference; the hydrophilic absorbers consist of TERRA-SORB® granules with a dehydrated size range of 1 mm to 6 mm; and the liquid hydrating the hydrophilic absorbers consists primarily of 70 ml to 75 ml of water per gram of dehydrated TERRA-SORB® granules.

Other embodiments are within the scope of the claims.

For example, the bulk thermal resistance of a thermal therapy device can be tailored for a particular application by incorporating a controlled quantity of small diameter insulating beads, for example, plastic or styrofoam beads. This feature enables the therapy device to be used to apply thermal therapy to therapy sites, such as the face, that cannot tolerate very low temperatures.

Each of the embodiments described above can be used to apply heat therapy. For these applications, therapy device 10 can be pre-heated in a microwave or in a container of boiling water and subsequently applied to a therapy site on a patient. Also, conventional food preservatives can be included within pad 20 to inhibit the growth of microorganisms, such as bacteria and mold.

Still other embodiments are within the scope of the claims.

What is claimed is:

1. A thermal therapy device for applying thermal therapy to a therapy site on a patient's body comprising
a flexible, water-impermeable container conformable to the shape of the therapy site on the patient's body, and
a plurality of discrete, non-water-soluble, hydrophilic absorbers contained within said flexible container and hydrated with a liquid comprising water, wherein said hydrophilic absorbers remain in discrete form through repeated cycles of water freezing and melting, permitting the thermal device to be reused while retaining conformability to the shape of the therapy site on the patient's body.

2. The thermal therapy device of claim 1 wherein said hydrophilic absorbers are formed from discrete acrylic polymer granules.

3. The thermal therapy device of claim 1 wherein said hydrophilic absorbers are formed from discrete cross-linked polyacrylamide copolymer granules.

4. The thermal therapy device of claim 1 wherein said hydrophilic absorbers are characterized in that water retained therein migrates out and freezes when subjected to a temperature of 32° F. to −20° F. and, when thawed, melted water is reabsorbed by said hydrophilic absorbers.

5. The thermal therapy device of claim 1 wherein said hydrophilic absorbers are in the size range of about 1 mm to about 6 mm when dehydrated.

6. A thermal therapy device for applying thermal therapy to a therapy site on a patient's body comprising
a flexible container conformable to the shape of the therapy site on the patient's body,
a plurality of discrete, non-water-soluble, hydrophilic absorbers contained within said flexible container and hydrated with a liquid comprising water, and
means for decreasing water mobility out of said hydrophilic absorbers,
wherein said hydrophilic absorbers remain in discrete form through repeated cycles of water freezing and melting, permitting the thermal device to be reused while retaining conformability to the shape of the therapy site on the patient's body.

7. The thermal therapy device of claim 6 wherein the flexible container is impermeable to water.

8. A thermal therapy device for applying thermal therapy to a therapy site on a patient's body comprising
a flexible container conformable to the shape of the therapy site on the patient's body, and
a plurality of discrete, non-water-soluble, hydrophilic absorbers contained within said flexible container and hydrated with a liquid comprising a mixture of water and humectant selected to decrease the mobility of water out of said hydrophilic absorbers,
wherein said hydrophilic absorbers remain in discrete form through repeated cycles of water freezing and melting, permitting the thermal device to be reused while retaining conformability to the shape of the therapy site on the patient's body.

9. The thermal therapy device of claim 8 wherein the humectant is selected from the group consisting of propylene glycol, ethylene glycol, glycerin, dimethyl sulfoxide, dimethyl formamide, and combinations thereof.

10. The thermal therapy device of claim 8 wherein the flexible container is impermeable to water.

11. The thermal therapy device of claim 1 wherein said liquid consists of a mixture of water and propylene glycol.

12. The thermal therapy device of claim 11 wherein the amount of propylene glycol in said solution is between about 1.5 ml to about 17.5 ml per gram of dehydrated absorbers.

13. The thermal therapy device of claim 11 wherein the amount of propylene glycol in said solution is between about 3.5 ml to about 4.5 ml per gram of dehydrated absorbers.

14. A thermal therapy device for applying thermal therapy to a therapy site on a patient's body comprising
a flexible container conformable to the shape of the therapy site on the patient's body, said container comprising an air passage allowing air to pass in and out of said container, and
a plurality of discrete, non-water-soluble, hydrophilic absorbers contained within said flexible container and hydrated with a liquid comprising water,
wherein said hydrophilic absorbers remain in discrete form through repeated cycles of water freezing and melting, permitting the thermal device to be reused while retaining conformability to the shape of the therapy site on the patient's body.

15. The thermal therapy device of claim 14 wherein said air passage is covered by an air permeable membrane.

16. The thermal therapy device of claim 15 wherein said air permeable membrane is formed from a hydrophobic and oleophobic material.

17. The thermal therapy device of claim 14 wherein the flexible container is impermeable to water.

18. A thermal therapy device for applying thermal therapy to a therapy site on a patient's body comprising
a flexible container conformable to the shape of the therapy site on the patient's body,
a plurality of discrete, non-water-soluble, hydrophilic absorbers contained within said flexible container and hydrated with a liquid comprising water, and
a plurality of hydrophobic beads contained within said container for increasing the bulk thermal resistance through said thermal therapy devices,
wherein said hydrophilic absorbers remain in discrete form through repeated cycles of water freezing and melting, permitting the thermal device to be reused while retaining conformability to the shape of the therapy site on the patient's body.

19. The thermal therapy device of claim 18 wherein the flexible container is impermeable to water.

20. A thermal therapy device for applying thermal therapy to a therapy site on a patient's body comprising
a plurality of discrete, non-water-soluble, hydrophilic absorbers hydrated with a liquid comprising water, said hydrophilic absorbers being contained within a flexible container conformable to the shape of the therapy site on the patient's body and comprising a pliable solid matrix suspending said hydrated hydrophilic absorbers,
wherein said hydrophilic absorbers remain in discrete form through repeated cycles of water freezing and melting, permitting the thermal device to be reused while retaining conformability to the shape of the therapy site on the patient's body.

21. The thermal therapy device of claim 20 wherein said flexible container is formed into an elongated wristrest useful for relieving pain associated with carpel tunnel syndrome.

22. The thermal therapy device of claim 20 wherein the flexible container is impermeable to water.

23. A thermal therapy device for applying thermal therapy to a therapy site on a patient's body comprising
a flexible container conformable to the shape of the therapy site on the patient's body,
a plurality of discrete, non-water-soluble, hydrophilic absorbers contained within said flexible container and hydrated with a liquid comprising water, and
a coloring agent which remains within said hydrophilic absorbers when frozen,
wherein said hydrophilic absorbers remain in discrete form through repeated cycles of water freezing and melting, permitting the thermal device to be reused while retaining conformability to the shape of the therapy site on the patient's body.

24. The thermal therapy device of claim 23 wherein the flexible container is impermeable to water.

25. The thermal therapy device of claim 1 further comprising a food preservative for inhibiting the growth of microorganisms inside said flexible container.

26. A thermal therapy device for applying thermal therapy to a therapy site on a patient's body comprising a flexible container conformable to the shape of the therapy site on the patient's body, a plurality of discrete, non-water-soluble cross-linked polyacrylamide copolymer granules hydrated with a solution consisting of water and a humectant selected from the group consisting of propylene glycol, ethylene glycol, glycerin, dimethyl sulfoxide, dimethyl formamide, and combinations thereof, and an air passage allowing air to pass in and out of said flexible container.

27. The thermal therapy device of claim 26 wherein said granules are in the size range of about 1 mm to about 6 mm when dehydrated.

28. The thermal therapy device of claim 26 wherein the selected humectant in said solution consists of propylene glycol in an amount of about 3.5 ml to about 4.5 ml per gram of said granules when dehydrated.

29. The thermal therapy device of claim 26 wherein the flexible container is impermeable to water.

30. A method for making a thermal therapy device for applying thermal therapy to a therapy site on a patient's body comprising the steps of:

providing a flexible container conformable to the shape of the therapy site on the patient's body;

placing within the container a plurality of discrete, non-water-soluble, hydrophilic absorbers; and hydrating the hydrophilic absorbers with a liquid comprising water and a humectant selected to decrease water mobility out of said hydrophilic absorbers.

31. The method of claim 30 wherein the hydrophilic absorbers placed within the container are formed from discrete cross-linked polyacrylamide copolymer granules.

32. The method of claim 31 wherein the humectant is selected from the group consisting of propylene glycol, ethylene glycol, glycerin, dimethyl sulfoxide, dimethyl formamide, and combinations thereof.

33. The method of claim 30 further comprising the step of providing an air passage through the flexible container to enable air to pass in and out of the flexible container.

34. The method of claim 30 wherein the hydrophilic absorbers are hydrated before being placed within the container, and wherein the container comprises a pliable solid matrix suspending the hydrated hydrophilic absorbers.

35. The method of claim 30 wherein the flexible container that is provided is impermeable to water.

36. A thermal therapy device for applying thermal therapy to a site on a human body, comprising a flexible structure impermeable to a phase change fluid and conformable to a shape of the site, the flexible structure comprising discrete absorbers that have an affinity for the phase change fluid but are not soluble in the phase change fluid, the absorbers being infused with the phase change fluid, the absorbers remaining discrete through repeated cycles of phase change of the phase change fluid.

37. A thermal therapy device for applying thermal therapy to a therapy site on a patient's body comprising a flexible, water-impermeable container conformable to the shape of the therapy site on the patient's body, a plurality of discrete, non-water-soluble, hydrophilic absorbers contained within said flexible container and hydrated with a liquid comprising water, and a plurality of discrete hydrophobic bodies contained within said flexible container.

38. The thermal therapy device of claim 37 wherein said hydrophobic bodies have the form of hydrophobic beads.

39. The thermal therapy device of claim 37 wherein said hydrophobic bodies are formed from Styrofoam.

40. The thermal therapy device of claim 37 wherein said hydrophobic bodies are formed from a plastic.

41. The thermal therapy device of claim 37 wherein said liquid comprises a mixture of water and a humectant.

42. The thermal therapy device of claim 41 wherein said humectant comprises propylene glycol.

43. The thermal therapy device of claim 37 wherein said hydrophilic absorbers comprise discrete acrylic polymer granules.

44. The thermal therapy device of claim 37 wherein said hydrophilic absorbers comprise discrete cross-linked polyacrylamide copolymer granules.

* * * * *